US012029470B2

(12) United States Patent
Heckel (10) Patent No.: US 12,029,470 B2
(45) Date of Patent: *Jul. 9, 2024

(54) SIMULTANEOUS RF MONOPOLAR CALIBRATION USING A SHARED RETURN ELECTRODE

(71) Applicant: Covidien LP, Mansfield, MA (US)

(72) Inventor: Donald W. Heckel, Thornton, CO (US)

(73) Assignee: Covidien LP, Mansfield, MA (US)

(*) Notice: Subject to any disclaimer, the term of this patent is extended or adjusted under 35 U.S.C. 154(b) by 401 days.

This patent is subject to a terminal disclaimer.

(21) Appl. No.: 17/318,050

(22) Filed: May 12, 2021

(65) Prior Publication Data

US 2021/0361338 A1 Nov. 25, 2021

Related U.S. Application Data

(60) Provisional application No. 63/028,012, filed on May 21, 2020, provisional application No. 63/028,049, (Continued)

(51) Int. Cl.
*A61B 18/12* (2006.01)
*A61B 18/16* (2006.01)
(Continued)

(52) U.S. Cl.
CPC .......... *A61B 18/1206* (2013.01); *A61B 18/16* (2013.01); *A61B 2017/00725* (2013.01); *A61B 2018/00642* (2013.01)

(58) Field of Classification Search
CPC ................ A61B 18/1206; A61B 18/16; A61B 2017/00725; A61B 2018/00642;
(Continued)

(56) References Cited

U.S. PATENT DOCUMENTS 37,165 A 12/1862 Gary
3,209,754 A 10/1965 Brown
(Continued)

FOREIGN PATENT DOCUMENTS

CN 101683284 A 3/2010
CN 102648864 A 8/2012
(Continued)

OTHER PUBLICATIONS

Detemple, P., "Microtechnology in Modern Health Care", Med Device Technol. 9(9):18-25 (1998).
(Continued)

*Primary Examiner* — Michael F Peffley
*Assistant Examiner* — Samantha M Good
(74) *Attorney, Agent, or Firm* — Carter, DeLuca & Farrell LLP (57) ABSTRACT

An electrosurgical generator includes a first radio frequency source having a first power supply configured to output a first direct current waveform; a first radio frequency inverter coupled to the first power supply and configured to generate a first radio frequency waveform from the first direct current waveform; and a first controller configured to control the first radio frequency inverter. The electrosurgical generator also includes a second radio frequency source having: a second power supply configured to output a second direct current waveform; a second radio frequency inverter coupled to the second power supply and configured to generate a second radio frequency waveform simultaneously as the first radio frequency waveform; and a second controller configured to control the second radio frequency inverter.

11 Claims, 8 Drawing Sheets

Related U.S. Application Data filed on May 21, 2020, provisional application No. 63/028,007, filed on May 21, 2020, provisional application No. 63/028,009, filed on May 21, 2020.

(51) Int. Cl.
*A61B 17/00* (2006.01)
*A61B 18/00* (2006.01)

(58) Field of Classification Search
CPC ........... A61B 2018/00779; A61B 2018/00827; A61B 2018/00875; A61B 2018/00892; A61B 2018/1253; A61B 2018/1293
See application file for complete search history.

(56) References Cited

U.S. PATENT DOCUMENTS

| | | |
|---|---|---|
| 3,273,562 A | 9/1966 | Brown |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,731,058 A | 3/1988 | Doan |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,391,166 A | 2/1995 | Eggers |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |

(56) References Cited

U.S. PATENT DOCUMENTS

| | | |
|---|---|---|
| 5,676,674 A | 10/1997 | Bolanos et al. |
| 5,680,981 A | 10/1997 | Mililli et al. |
| 5,680,982 A | 10/1997 | Schulze et al. |
| 5,690,675 A | 11/1997 | Sawyer et al. |
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,755,726 A | 5/1998 | Pratt et al. |
| 5,759,171 A | 6/1998 | Coelho et al. |
| 5,779,130 A | 7/1998 | Alesi et al. |
| 5,782,397 A | 7/1998 | Koukline |
| 5,785,713 A | 7/1998 | Jobe |
| 5,788,698 A | 8/1998 | Savornin |
| 5,810,811 A | 9/1998 | Yates et al. |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |
| 6,497,707 B1 | 12/2002 | Bowman et al. |
| 6,505,768 B2 | 1/2003 | Whitman |
| 6,515,273 B2 | 2/2003 | Al-Ali |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnside et al. |
| 6,616,821 B2 | 9/2003 | Broadley et al. |
| 6,629,986 B1 | 10/2003 | Ross et al. |
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,792,390 B1 | 9/2004 | Burnside et al. |
| 6,793,652 B1 | 9/2004 | Whitman et al. |

(56) References Cited

U.S. PATENT DOCUMENTS

| | | |
|---|---|---|
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Al-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,670,334 B2 | 3/2010 | Hueil et al. |
| 7,694,809 B2 | 4/2010 | Garbini et al. |
| 7,721,931 B2 | 5/2010 | Shelton, IV et al. |
| 7,740,159 B2 | 6/2010 | Shelton, IV et al. |
| 7,753,248 B2 | 7/2010 | Viola |
| 7,757,925 B2 | 7/2010 | Viola et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,784,663 B2 | 8/2010 | Shelton, IV |
| 7,815,090 B2 | 10/2010 | Marczyk |
| 7,823,760 B2 | 11/2010 | Zemlok et al. |
| 7,845,534 B2 | 12/2010 | Viola et al. |
| 7,870,989 B2 | 1/2011 | Viola et al. |
| 7,886,953 B2 | 2/2011 | Schwemberger et al. |
| 7,887,530 B2 | 2/2011 | Zemlok et al. |
| 7,905,897 B2 | 3/2011 | Whitman et al. |
| 7,909,221 B2 | 3/2011 | Viola et al. |
| 7,922,063 B2 | 4/2011 | Zemlok et al. |
| 7,931,660 B2 | 4/2011 | Aranyi et al. |
| 7,950,560 B2 | 5/2011 | Zemlok et al. |
| 7,955,352 B2 | 6/2011 | McEwen et al. |
| 8,006,885 B2 | 8/2011 | Marczyk |
| 8,006,887 B2 | 8/2011 | Marczyk |
| 8,011,551 B2 | 9/2011 | Marczyk et al. |
| 8,020,742 B2 | 9/2011 | Marczyk |
| 8,025,199 B2 | 9/2011 | Whitman et al. |
| 8,038,044 B2 | 10/2011 | Viola |
| 8,052,024 B2 | 11/2011 | Viola et al. |
| 8,066,721 B2 | 11/2011 | Kortenbach et al. |
| 8,074,858 B2 | 12/2011 | Marczyk |
| 8,092,493 B2 | 1/2012 | Marczyk |
| 8,128,645 B2 | 3/2012 | Sonnenschein et al. |
| 8,132,705 B2 | 3/2012 | Viola et al. |
| 8,157,150 B2 | 4/2012 | Viola et al. |
| 8,186,555 B2 | 5/2012 | Shelton, IV et al. |
| 8,201,721 B2 | 6/2012 | Zemlok et al. |
| 8,210,412 B2 | 7/2012 | Marczyk |
| 8,240,536 B2 | 8/2012 | Marczyk |
| 8,240,537 B2 | 8/2012 | Marczyk |
| 8,267,924 B2 | 9/2012 | Zemlok et al. |
| 8,328,823 B2 | 12/2012 | Aranyi et al. |
| 8,348,125 B2 | 1/2013 | Viola et al. |
| 8,685,004 B2 | 4/2014 | Zemlock et al. |
| 9,192,381 B2 | 11/2015 | Marczyk |
| 9,364,222 B2 | 6/2016 | Zemlok et al. |
| 9,370,360 B2 | 6/2016 | Marczyk |
| 9,370,361 B2 | 6/2016 | Viola et al. |
| 9,433,415 B2 | 9/2016 | Marczyk et al. |
| 9,480,492 B2 | 11/2016 | Aranyi et al. |
| 9,480,523 B2 * | 11/2016 | Heckel ............... A61B 18/1206 |
| 9,585,659 B2 | 3/2017 | Viola et al. |
| 10,492,814 B2 | 12/2019 | Snow et al. |
| 10,610,287 B2 | 4/2020 | Dunning |
| 10,722,222 B2 | 7/2020 | Aranyi |
| 2002/0103489 A1 | 8/2002 | Ku |
| 2002/0111641 A1 | 8/2002 | Peterson et al. |
| 2002/0165541 A1 | 11/2002 | Whitman |
| 2003/0090201 A1 | 5/2003 | Peng |
| 2003/0114851 A1 | 6/2003 | Truckai et al. |
| 2003/0120306 A1 | 6/2003 | Burbank et al. |
| 2004/0232201 A1 | 11/2004 | Wenchell et al. |
| 2005/0006429 A1 | 1/2005 | Wales et al. |
| 2005/0010235 A1 | 1/2005 | VanDusseldorp |
| 2005/0131390 A1 | 6/2005 | Heinrich et al. |
| 2005/0139636 A1 | 6/2005 | Schwemberger et al. |
| 2005/0177176 A1 | 8/2005 | Gerbi et al. |
| 2005/0192609 A1 | 9/2005 | Whitman et al. |
| 2005/0247753 A1 | 11/2005 | Kelly et al. |
| 2006/0000867 A1 | 1/2006 | Shelton et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |

(56) References Cited

U.S. PATENT DOCUMENTS

| | | |
|---|---|---|
| 2007/0219563 A1 | 9/2007 | Voegele |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0135600 A1 | 6/2008 | Hiranuma et al. |
| 2008/0169329 A1 | 7/2008 | Shelton et al. |
| 2008/0185419 A1 | 8/2008 | Smith et al. |
| 2008/0197167 A1 | 8/2008 | Viola et al. |
| 2008/0255413 A1 | 10/2008 | Zemlok et al. |
| 2008/0255607 A1 | 10/2008 | Zemlok |
| 2008/0281322 A1* | 11/2008 | Sherman ............ A61B 18/1206 606/42 |
| 2009/0018624 A1 | 1/2009 | Levinson et al. |
| 2009/0090201 A1 | 4/2009 | Viola |
| 2009/0090763 A1 | 4/2009 | Zemlok et al. |
| 2010/0200636 A1 | 8/2010 | Zemlok et al. |
| 2010/0312257 A1 | 12/2010 | Aranyi |
| 2010/0320254 A1 | 12/2010 | Zemlok et al. |
| 2011/0034910 A1 | 2/2011 | Ross et al. |
| 2011/0062211 A1 | 3/2011 | Ross et al. |
| 2011/0168757 A1 | 7/2011 | Viola et al. |
| 2011/0172681 A1 | 7/2011 | Aranyi et al. |
| 2011/0190738 A1 | 8/2011 | Zemlok et al. |
| 2011/0301579 A1 | 12/2011 | Marczyk et al. |
| 2011/0303735 A1 | 12/2011 | Marczyk |
| 2012/0055972 A1 | 3/2012 | Marczyk |
| 2012/0074197 A1 | 3/2012 | Marczyk |
| 2012/0175400 A1 | 7/2012 | Viola et al. |
| 2012/0193393 A1 | 8/2012 | Viola et al. |
| 2012/0198288 A1 | 8/2012 | Njo et al. |
| 2012/0220989 A1 | 8/2012 | Zemlok et al. |
| 2012/0223121 A1 | 9/2012 | Viola et al. |
| 2012/0241494 A1 | 9/2012 | Marczyk |
| 2012/0277790 A1 | 11/2012 | Zemlok et al. |
| 2012/0298718 A1 | 11/2012 | Marczyk |
| 2012/0298720 A1 | 11/2012 | Marczyk |
| 2019/0132062 A1* | 5/2019 | Heckel ................. H04B 17/345 |
| 2021/0361339 A1* | 11/2021 | Heckel ................. A61B 18/16 |

FOREIGN PATENT DOCUMENTS

| | | |
|---|---|---|
| EP | 0537570 A2 | 4/1993 |
| EP | 0647431 A2 | 4/1995 |
| EP | 0738501 A1 | 10/1996 |
| EP | 0770354 A1 | 5/1997 |
| EP | 1070487 A2 | 1/2001 |
| EP | 1201196 A1 | 5/2002 |
| EP | 1658817 A1 | 5/2006 |
| EP | 1813203 A2 | 8/2007 |
| EP | 2679184 B1 | 4/2015 |
| FR | 2 849 589 A1 | 7/2004 |
| WO | 9414129 A1 | 6/1994 |
| WO | 9729694 A1 | 8/1997 |
| WO | 9740760 A1 | 11/1997 |
| WO | 9837825 A1 | 9/1998 |
| WO | 1999/52489 A1 | 10/1999 |
| WO | 0234140 A2 | 5/2002 |
| WO | 03026511 A1 | 4/2003 |
| WO | 03030743 A2 | 4/2003 |
| WO | 2004032760 A2 | 4/2004 |
| WO | 2007030753 A2 | 3/2007 |
| WO | 2007/114868 A2 | 10/2007 |
| WO | 2007118179 A2 | 10/2007 |
| WO | 2007014355 A3 | 4/2009 |
| WO | 2009143092 A1 | 11/2009 |

OTHER PUBLICATIONS

Abridged Data Sheet, "DeepCover Secure Authenticator with 1-Wire SHA-256 and 512-Bit User EEPROM", Maxim Integrated Products, Inc. pp 1-4; 42; Dec. 2012.

Data Sheet "DS28E151—Sire SHA-256 Secure Authenticator with 512-Bit User EEPROM" ; IC-ON-LINE, Electronic Component Manufacturers, pp. 1-2; Aug. 2013.

Extended European Search Report dated Oct. 19, 2021 issued in corresponding EP Appln. No. 21175382.7.

* cited by examiner

SIMULTANEOUS RF MONOPOLAR CALIBRATION USING A SHARED RETURN ELECTRODE

CROSS-REFERENCE TO RELATED APPLICATIONS

The present application claims the benefit of and priority to U.S. Provisional Patent Applications Nos. 63/028,009, 63/028,012, 63/028,007, and 63/028,049, each of which were filed on May 21, 2020. The entire contents of each of the foregoing applications are incorporated by reference herein.

BACKGROUND

Technical Field

The present disclosure relates to systems and methods for controlling an electrosurgical generator. In particular, the present disclosure relates to controlling a plurality of monopolar electrosurgical devices that share a common return path through one or more return electrodes.

Background of Related Art

Electrosurgery involves application of high radio frequency electrical current to a surgical site to cut, ablate, desiccate, or coagulate tissue. In monopolar electrosurgery, a source or active electrode delivers radio frequency alternating current from the electrosurgical generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes.

The current solution for dual site surgery, namely, using two electrosurgical instruments simultaneously, is generally to use two electrosurgical generators. This solution is inherently cumbersome and cost prohibitive. Thus, there is a need for independent control of the multiple ports of a single electrosurgical generator using a common return path.

SUMMARY

The present disclosure provides an electrosurgical system including an electrosurgical generator having two radio frequency (RF) channels generated by two separate RF sources. Each of the sources includes a power supply configured to output DC power and an RF power inverter configured to output an RF waveform. The individual RF waveform is supplied to a corresponding monopolar instrument and each RF waveform is returned through a common return path, which may include one or more return electrode pads. Each of the sources is controlled by its own controller, each of which is coupled to a common clock source. The electrosurgical generator performs a wide band measurement of each source's monopolar discontinuous or continuous signal simultaneously detecting cross-conductance (e.g., cross-talk) between the RF sources.

According to one embodiment of the present disclosure, an electrosurgical calibration system is disclosed. The electrosurgical calibration system includes an electrosurgical generator having a first radio frequency source, which includes a first power supply configured to output a first direct current waveform; a first radio frequency inverter coupled to the first power supply and configured to generate a first radio frequency waveform from the first direct current waveform; a first active terminal coupled to the first radio frequency inverter; and a first controller configured to control the first radio frequency inverter. The electrosurgical generator further includes a second radio frequency source having a second power supply configured to output a second direct current waveform; a second radio frequency inverter coupled to the second power supply and configured to generate a second radio frequency waveform simultaneously as the first radio frequency waveform; a second active terminal coupled to the second radio frequency inverter; and a second controller configured to control the second radio frequency inverter. The electrosurgical generator further includes a common return terminal coupled to the first radio frequency inverter and the second radio frequency inverter. The electrosurgical calibration system further includes a calibration assembly having a first active connector configured to couple to the first active terminal; a second active connector configured to couple to the second active terminal; and a return connector configured to couple to the common return terminal, wherein the calibration assembly is configured to measure at least one electrical property in response to the first and second radio frequency waveforms.

According to one aspect of the above embodiment, the calibration assembly further includes a first contact impedance portion configured to simulate impedance at a point of contact between tissue and a first electrosurgical instrument coupled to the first active terminal. The first contact impedance portion includes a first resistor having a resistance from about 100 Ohms to about 2,000 Ohms. The calibration assembly further includes a second contact impedance portion configured to simulate impedance at a point of contact between tissue and a second electrosurgical instrument coupled to the second active terminal. The second contact impedance portion includes a second resistor having a resistance from about 100 Ohms to about 2,000 Ohms. The calibration assembly further includes return electrode impedance portion configured simulate impedance at a point of contact between tissue and a return electrode pad coupled to the common return terminal. The return electrode impedance portion includes a pair of resistors configured to simulate a pair of foil electrodes of the return electrode pad.

According to another aspect of the above embodiment, the calibration assembly includes a plurality of resistors configured to simulate impedance at points of contact between a return electrode pad to the common return terminal, a first electrosurgical instrument coupled to the first active terminal, and a second electrosurgical instrument coupled to the second active terminal. The plurality of resistors are variable resistors whose resistances are adjusted by the calibration assembly. The calibration assembly includes at least one sensor configured to measure an electrical property of the calibration assembly. Each of the first controller and the second controller is configured to calculate a calibration value based on the electrical property.

BRIEF DESCRIPTION OF THE DRAWINGS

The present disclosure may be understood by reference to the accompanying drawings, when considered in conjunction with the subsequent, detailed description, in which.

DETAILED DESCRIPTION

Embodiments of the presently disclosed electrosurgical system are described in detail with reference to the drawings, in which like reference numerals designate identical or corresponding elements in each of the several views. As used herein the term "distal" refers to the portion of the surgical instrument coupled thereto that is closer to the patient, while the term "proximal" refers to the portion that is farther from the patient.

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller, or on a user device, including, for example, a mobile device, an IOT device, a server system, or any programmable logic device.

In the following description, well-known functions or constructions are not described in detail to avoid obscuring the present disclosure in unnecessary detail. Those skilled in the art will understand that the present disclosure may be adapted for use with either an endoscopic instrument, a laparoscopic instrument, or an open instrument. It should also be appreciated that different electrical and mechanical connections and other considerations may apply to each particular type of instrument.

An electrosurgical generator according to the present disclosure may be used in monopolar and/or bipolar electrosurgical procedures, including, for example, cutting, coagulation, ablation, and vessel sealing procedures. The generator may include a plurality of outputs for interfacing with various ultrasonic and electrosurgical instruments (e.g., ultrasonic dissectors and hemostats, monopolar instruments, return electrode pads, bipolar electrosurgical forceps, footswitches, etc.). Further, the generator may include electronic circuitry configured to generate radio frequency energy specifically suited for powering ultrasonic instruments and electrosurgical devices operating in various electrosurgical modes (e.g., cut, blend, coagulate, division with hemostasis, fulgurate, spray, etc.) and procedures (e.g., monopolar, bipolar, vessel sealing).

The present disclosure provides an electrosurgical generator having two radio frequency (RF) channels generated by two separate RF sources. Each of the sources includes a power supply configured to output DC power and an RF power inverter configured to output an RF waveform. The individual RF waveform is supplied to a corresponding monopolar instrument and each RF waveform is returned through a common return path, which may include one or more return electrode pads.

Conventional monopolar electrosurgical generators may be calibrated at a particular impedance with a resistive load coupled to (e.g., wired between) an active electrode (e.g., instrument) and a return electrode (e.g., electrode pad). The present disclosure provides a novel calibration assembly for use with dual RF source generator, which compensate for the tissue between two active electrodes and for the common return path.

Figure 1:
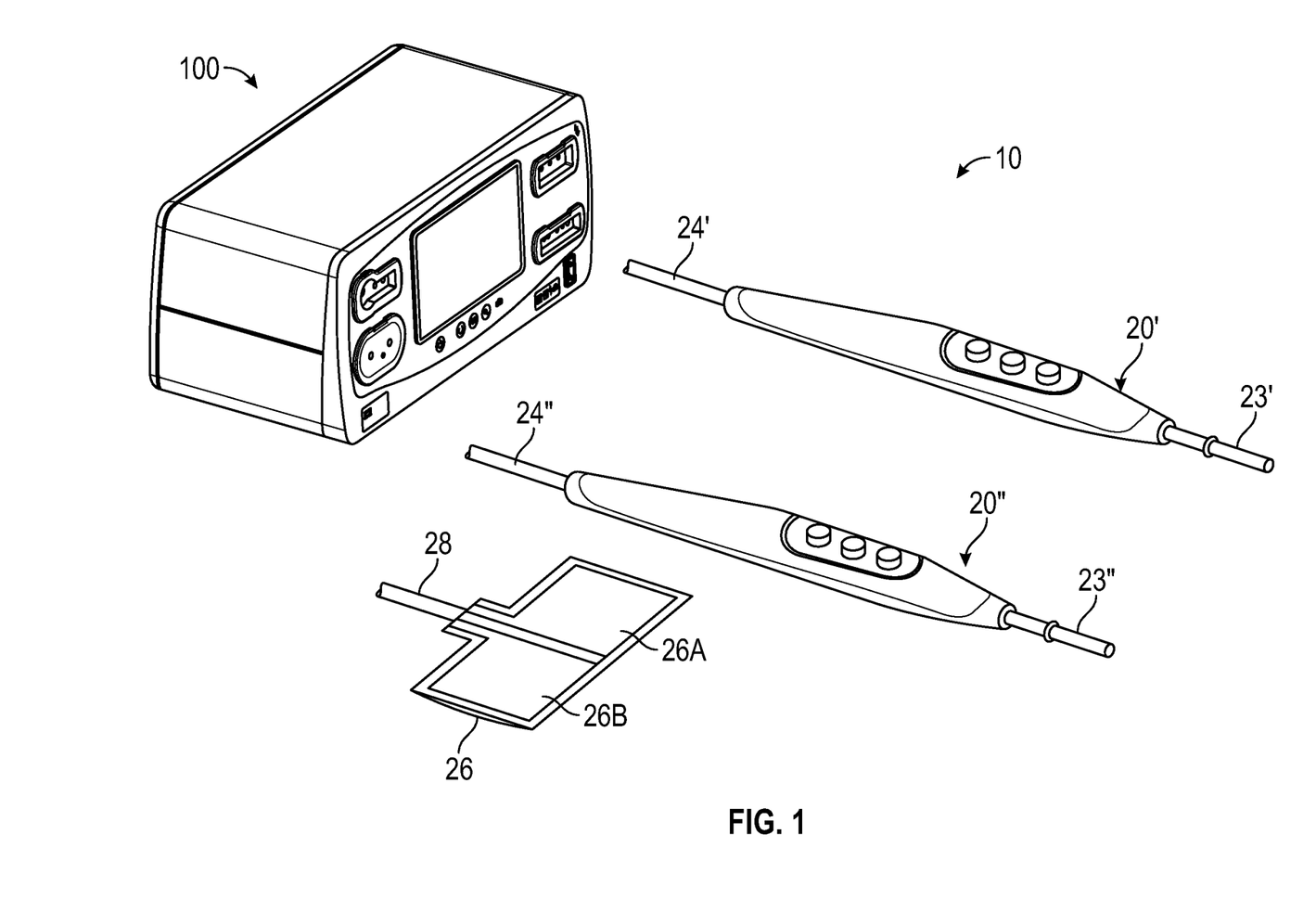
FIG. 1 is a perspective view of an electrosurgical system according to an embodiment of the present disclosure.

Referring to FIG. 1 an electrosurgical system 10 is shown which includes one or more monopolar electrosurgical instruments 20' and 20" having one or more active electrodes 23' and 23" (e.g., electrosurgical cutting probe, ablation electrode(s), etc.) for treating tissue of a patient. The system 10 may include a plurality of return electrode pads 26 that, in use, are disposed on a patient to minimize the chances of tissue damage by maximizing the overall contact area with the patient. Electrosurgical alternating RF current is supplied to the instruments 20' and 20" by a generator 100 via supply lines 24' and 24". The generator 100 is a dual source RF generator configured to supply a separate RF waveform to each of the instruments 20' and 20" from individual RF sources. The alternating RF current is returned to the generator 100 through the return electrode pad 26 via a return line 28. In addition, the generator 100 and the return electrode pads 26 may be configured for monitoring tissue-to-patient contact to ensure that sufficient contact exists therebetween. In particular, the return electrode pad 26 includes a pair of foil electrodes 26a and 26b, which are used to monitor tissue-to-patient contact by detecting a difference in electrical properties of the foil electrodes 26a and 26b.

Figure 2:
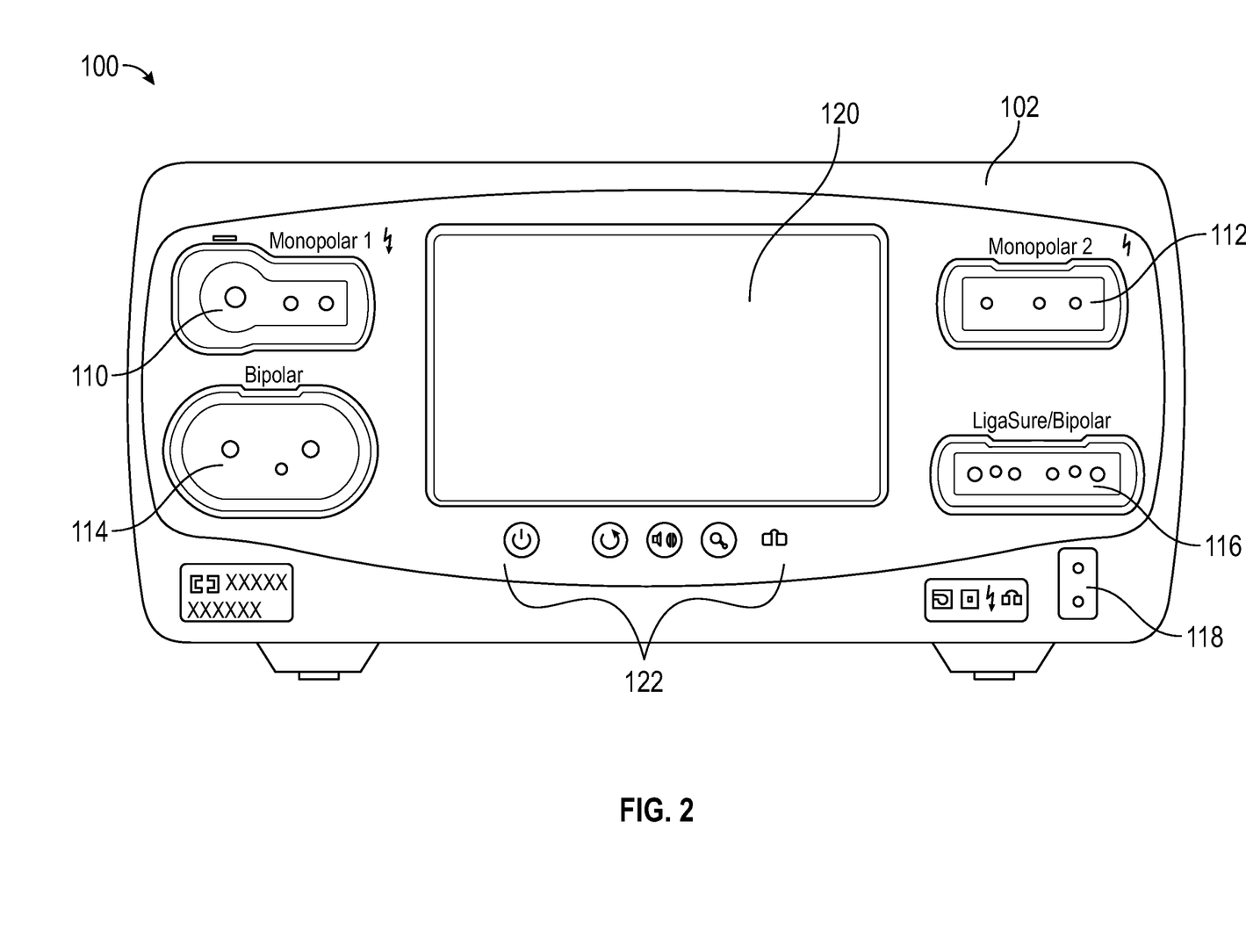
FIG. 2 is a front view of a dual RF source electrosurgical generator of FIG. 1 according to an embodiment of the present disclosure.

With reference to FIG. 2, a front face 102 of the generator 100 is shown. The generator 100 may include a plurality of ports 110, 112, 114, 116 to accommodate various types of electrosurgical instruments and a port 118 for coupling to the return electrode pad 26. The generator 100 includes a display 120 for providing the user with variety of output information (e.g., intensity settings, treatment complete indicators, etc.). The display 120 is a touchscreen configured to display a corresponding menu for the instruments (e.g., more monopolar electrosurgical instruments 20' and 20", electrosurgical forceps, etc.). The user then adjusts inputs by simply touching corresponding menu options. The generator 100 also includes suitable input controls 122 (e.g., buttons, activators, switches, touch screen, etc.) for controlling the generator 100.

The generator 100 is configured to operate in a variety of modes and is configured to output a monopolar waveform, which is based on the selected mode. In embodiments, the generator 100 may operate in the following modes, which include, but are not limited to, cut, blend, division with hemostasis, fulgurate and spray. Each of the modes operates based on a preprogrammed power curve that dictates how much power is output by the generator 100 at varying impedance ranges of the load (e.g., tissue). Each of the power curves includes power, voltage and current control ranges that are defined by the user-selected intensity setting and the measured minimum impedance of the load.

The first and second RF waveforms may be either continuous or discontinuous and may have a carrier frequency from about 200 kHz to about 500 kHz. As used herein, continuous waveforms are waveforms that have a 100% duty cycle. In embodiments, continuous waveforms are used to impart a cutting effect on tissue. Conversely, discontinuous waveforms are waveforms that have a non-continuous duty cycle, e.g., below 100%. In embodiments, discontinuous waveforms are used to provide coagulation effects to tissue.

In the cut mode, the generator 100 may supply a continuous sine waveform at a predetermined carrier frequency (e.g., 472 kHz) having a crest factor of about 1.5 with an impedance of from about 100Ω to about 2,000Ω. The cut mode power curve may include three regions: constant current into low impedance, constant power into medium impedance and constant voltage into high impedance. In the blend mode, the generator may supply bursts of a sine waveform at the predetermined frequency, with the bursts reoccurring at a first predetermined rate (e.g., about 26.21 kHz). In one embodiment, the duty cycle of the bursts may be about 50%. The crest factor of one period of the sine waveform may be about 1.5. The crest factor of the burst may be about 2.7.

The division with hemostasis mode may include bursts of sine waveforms at a predetermined frequency (e.g., 472 kHz) reoccurring at a second predetermined rate (e.g., about 28.3 kHz). The duty cycle of the bursts may be about 25%. The crest factor of one burst may be about 4.3 across an impedance of from about 100Ω to about 2,000Ω. The fulgurate mode may include bursts of sine waveforms at a predetermined frequency (e.g., 472 kHz) reoccurring at a third predetermined rate (e.g., about 30.66 kHz). The duty cycle of the bursts may be about 6.5% and the crest factor of one burst cycle may be about 5.55 across an impedance range of from about 100Ω to about 2,000Ω. The spray mode may include bursts of sine waveform at a predetermined frequency (e.g., 472 kHz) reoccurring at a fourth predetermined rate (e.g., about 21.7 kHz). The duty cycle of the bursts may be about 4.6% and the crest factor of one burst cycle may be about 6.6 across the impedance range of from about 100Ω to about 2,000Ω.

Figure 3:
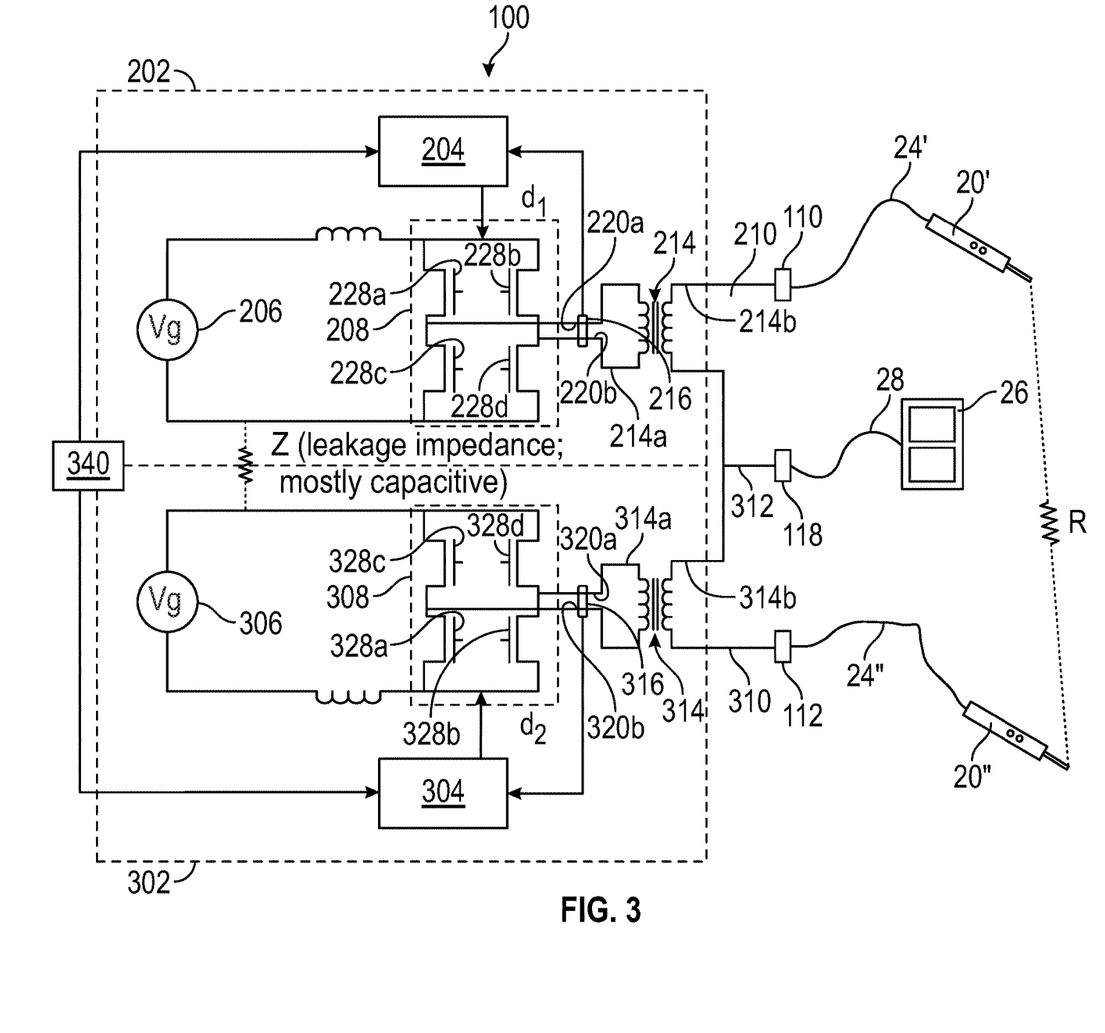
FIG. 3 is a schematic diagram of the electrosurgical generator of FIG. 1 according to an embodiment of the present disclosure.

With reference to FIG. 3, the generator 100 includes a dual source RF architecture, where each RF source is supplied by an individual and separate RF inverter, each of which is powered by an individual and separate DC power supply. More specifically, the generator 100 includes a first RF source 202 and a second RF source 302. Each of the sources 202 and 302 includes a first controller 204 and a second controller 304, a first power supply 206 and a second power supply 306, and a first RF inverter 208 and a second RF inverter 308. The power supplies 206 and 306 may be high voltage, DC power supplies connected to a common AC source (e.g., line voltage) and provide high voltage, DC power to their respective RF inverters 208 and 308, which then convert DC power into a first and second RF waveforms through their respective active terminals 210 and 310. The energy is returned thereto via a shared return terminal 312. In particular, electrosurgical energy for energizing the monopolar electrosurgical instruments 20' and 20" coupled to ports 110 and 112 is delivered through the active terminals 210 and 310 and returned through the return electrode pad 26 coupled to the port 118, which in turn, is coupled to the return terminal 312.

The active terminal 210 and the return terminal 312 are coupled to the RF inverter 208 through an isolation transformer 214. The isolation transformer 214 includes a primary winding 214a coupled to the RF inverter 208 and a secondary winding 214b coupled to the active and return terminals 210 and 312. Similarly, the active terminal 310 and the return terminal 312 are coupled to the RF inverter 308 through an isolation transformer 314. The isolation transformer 314 includes a primary winding 314a coupled to the RF inverter 308 and a secondary winding 314b coupled to the active and return terminals 310 and 312.

The RF inverters 208 and 308 are configured to operate in a plurality of modes, during which the generator 100 outputs corresponding waveforms having specific duty cycles, peak voltages, crest factors, etc. It is envisioned that in other embodiments, the generator 100 may be based on other types of suitable power supply topologies. RF inverters 208 and 308 may be resonant RF amplifiers or non-resonant RF amplifiers, as shown. A non-resonant RF amplifier, as used herein, denotes an amplifier lacking any tuning components, i.e., conductors, capacitors, etc., disposed between the RF inverter and the load, e.g., tissue.

The controllers 204 and 304 may include a processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to perform the calculations and/or set of instructions described herein.

Each of the controllers 204 and 304 is operably connected to the respective power supplies 206 and 306 and/or RF inverters 208 and 308 allowing the processor to control the output of the first RF source 202 and the second RF source 302 of the generator 100 according to either open and/or closed control loop schemes. A closed loop control scheme is a feedback control loop, in which a plurality of sensors measures a variety of tissue and energy properties (e.g., tissue impedance, tissue temperature, output power, current and/or voltage, etc.), and provide feedback to each of the controllers 204 and 304. The controllers 204 and 304 then control their respective power supplies 206 and 306 and/or RF inverters 208 and 308, which adjust the DC and/or RF waveform, respectively.

The generator 100 according to the present disclosure may also include a plurality of sensors 216 and 316, each of which monitors output of the first RF source 202 and the second RF source 302 of the generator 100. The sensors 216 and 316 may be any suitable voltage, current, power, and impedance sensors. In the embodiment illustrated in FIG. 3, the sensors 216 are coupled to leads 220a and 220b of the RF inverter 208. The leads 220a and 220b couple the RF inverter 208 to the primary winding 214a of the transformer 214. The sensors 316 are coupled to leads 320a and 320b of the RF inverter 308. The leads 320a and 320b couple the RF inverter 308 to the primary winding 314a of the transformer 314. Thus, the sensors 216 and 316 are configured to sense voltage, current, and other electrical properties of energy supplied to the active terminals 210 and 310 and the return terminal 312.

In further embodiments, the sensors 216 and 316 may be coupled to the power supplies 206 and 306 and may be configured to sense properties of DC current supplied to the RF inverters 208 and 308. The controllers 204 and 304 also receive input signals from the display 120 and the input controls 122 of the generator 100 and/or the instruments 20' and 20". The controllers 204 and 304 adjust power outputted by the generator 100 and/or perform other control functions thereon in response to the input signals.

The RF inverters 208 and 308 includes a plurality of switching elements 228a-228d and 328a-328d, respectively, which are arranged in an H-bridge topology. In embodiments, RF inverters 208 and 308 may be configured according to any suitable topology including, but not limited to, half-bridge, full-bridge, push-pull, and the like. Suitable switching elements include voltage-controlled devices such as transistors, field-effect transistors (FETs), combinations thereof, and the like. In embodiments, the FETs may be formed from gallium nitride, aluminum nitride, boron nitride, silicone carbide, or any other suitable wide bandgap materials.

The controllers 204 and 304 are in communication with the respective RF inverters 208 and 308, and in particular, with the switching elements 228a-228d and 328a-328d. Controllers 204 and 304 are configured to output control signals, which may be pulse-width modulated ("PWM") signals, to switching elements 228a-228d and 328a-328d. In particular, controller 204 is configured to modulate a control signal d1 supplied to switching elements 228a-228d of the RF inverter 208 and the controller 304 is configured to modulate a control signal d2 supplied to switching elements 328a-328d of RF inverter 308. The control signals d1 and d2 provide PWM signals that operate the RF inverters 208 and 308 at their respective selected carrier frequency. Additionally, controller 204 and 304 are configured to calculate power characteristics of output of the first RF source 202 and the second RF source 302 of the generator 100, and control the output of the first RF source 202 and the second RF source 302 based at least in part on the measured power characteristics including, but not limited to, voltage, current, and power at the output of RF inverters 208 and 308.

Figure 4:
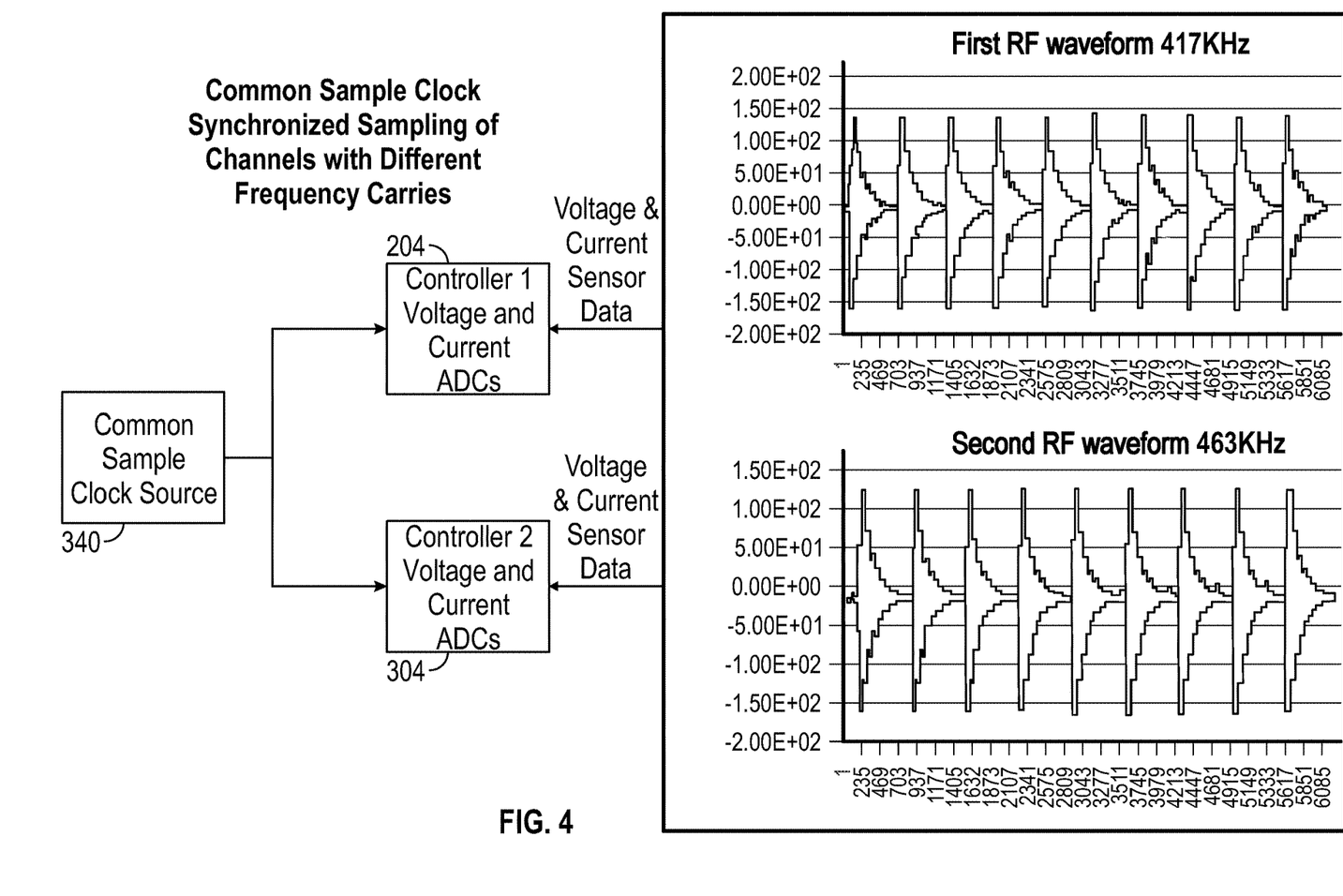
FIG. 4 is a schematic diagram of a clock source coupled to a first controller of a first RF source and a second controller of a second control source the electrosurgical generator of FIG. 1 according to the present disclosure.

With reference to FIGS. 3 and 4, each of the controllers 204 and 304 is coupled a clock source 340 which acts as a common frequency source for each of the controllers 204 and 304, such that the controllers 204 and 304 are synced. The clock source 340 is an electronic oscillator circuit that produces a clock signal for synchronizing operation of the controllers 204 and 304. Each of the controllers 204 and 304 generates an RF waveform based on clock signal from the clock source 340 and the selected mode. Thus, the once the user selects one of the electrosurgical modes, each of the controllers 204 and 304 outputs a first and second control signal, which are used to control the respective RF inverters 208 and 308 to output first and second RF waveforms corresponding to the selected mode. The selected mode for each of the first RF source 202 and the second RF source 302, and the corresponding RF waveforms, may be the same or different.

The RF waveforms have different carrier frequencies, such that the first RF waveform has a first carrier frequency and the second RF waveform has a second carrier frequency. The two different carrier frequencies are selected such that the controllers 204 and 304 can discriminate or separate measurement data in the frequency domain. The measurement data is collected by the sensors 216 and 316 which monitor the output of the first RF source 202 and the second RF source 302. The controllers 204 and 304 analyze their respective first and second RF waveforms using any suitable band pass technique or any technique which transforms the measurement data to the frequency domain, such as discrete Fourier transform (DFT) and fast Fourier transform (FFT). In embodiments, the controllers 204 and 304 may use arrays of Goertzel filters which are pointed to the carrier frequency and its harmonics of the RF waveform for continuous waveforms (e.g., those used during cut mode). With respect to discontinuous waveforms, the Goertzel filters are pointed to the repetition rate and harmonics of the carrier frequency of the waveform being analyzed. The filtering of measurement data may be performed by applications, e.g., software instructions, executable by the controllers 204 and 304.

Figure 5:
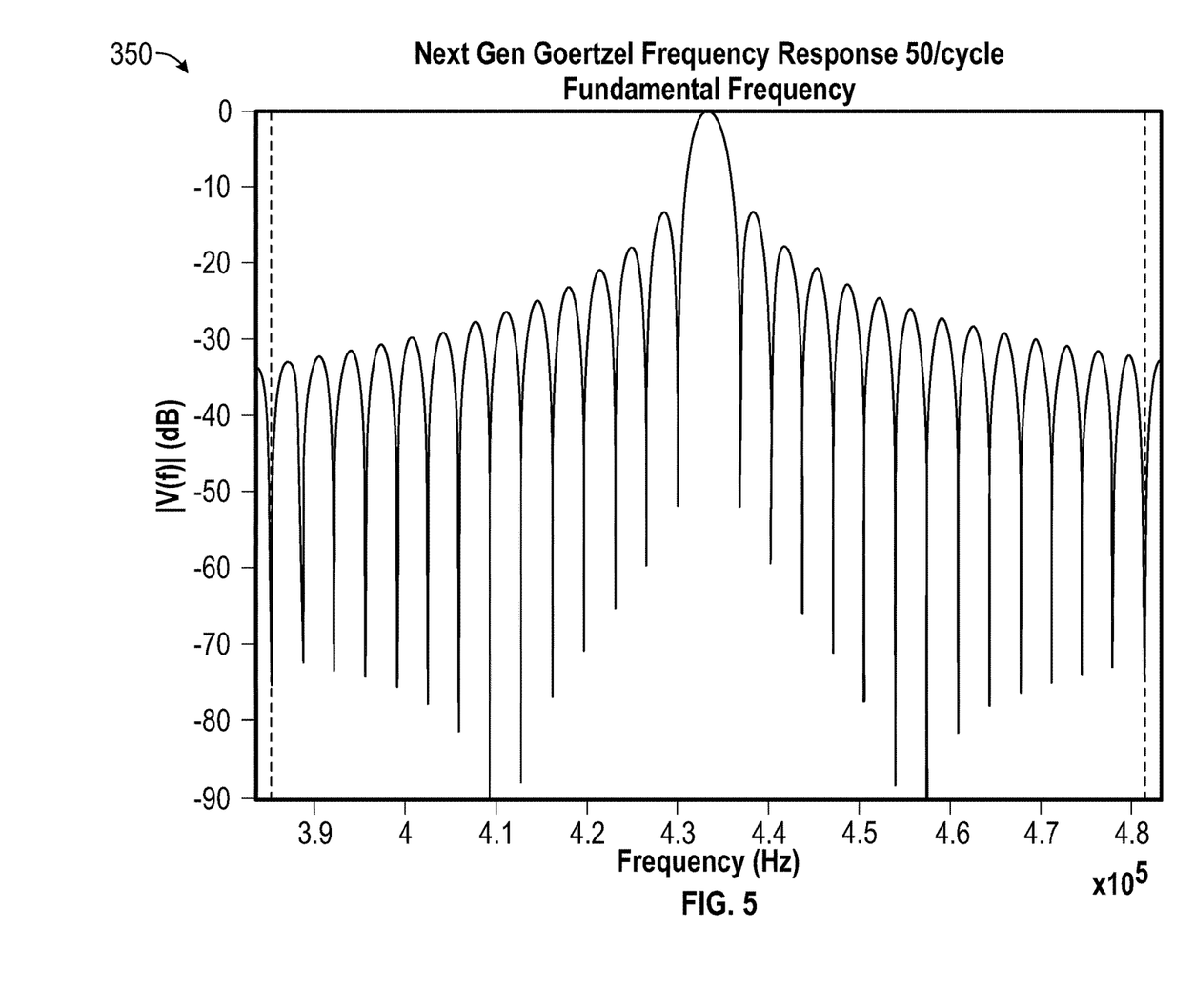
FIG. 5 is a frequency response plot of continuous RF waveforms generated by the electrosurgical generator of FIG. 1 according to the present disclosure.

The frequencies for the first and second RF waveforms are selected to provide sufficient channel separation between the carrier frequencies of the first RF waveform and the second RF waveform as determined by the band pass Goertzel filters. With reference to a frequency response plot 350 of FIG. 5, the opposite RF port frequencies for continuous waveforms are chosen to be at the null points of the frequency response. This maximizes the source-to-source separation.

Figure 6:
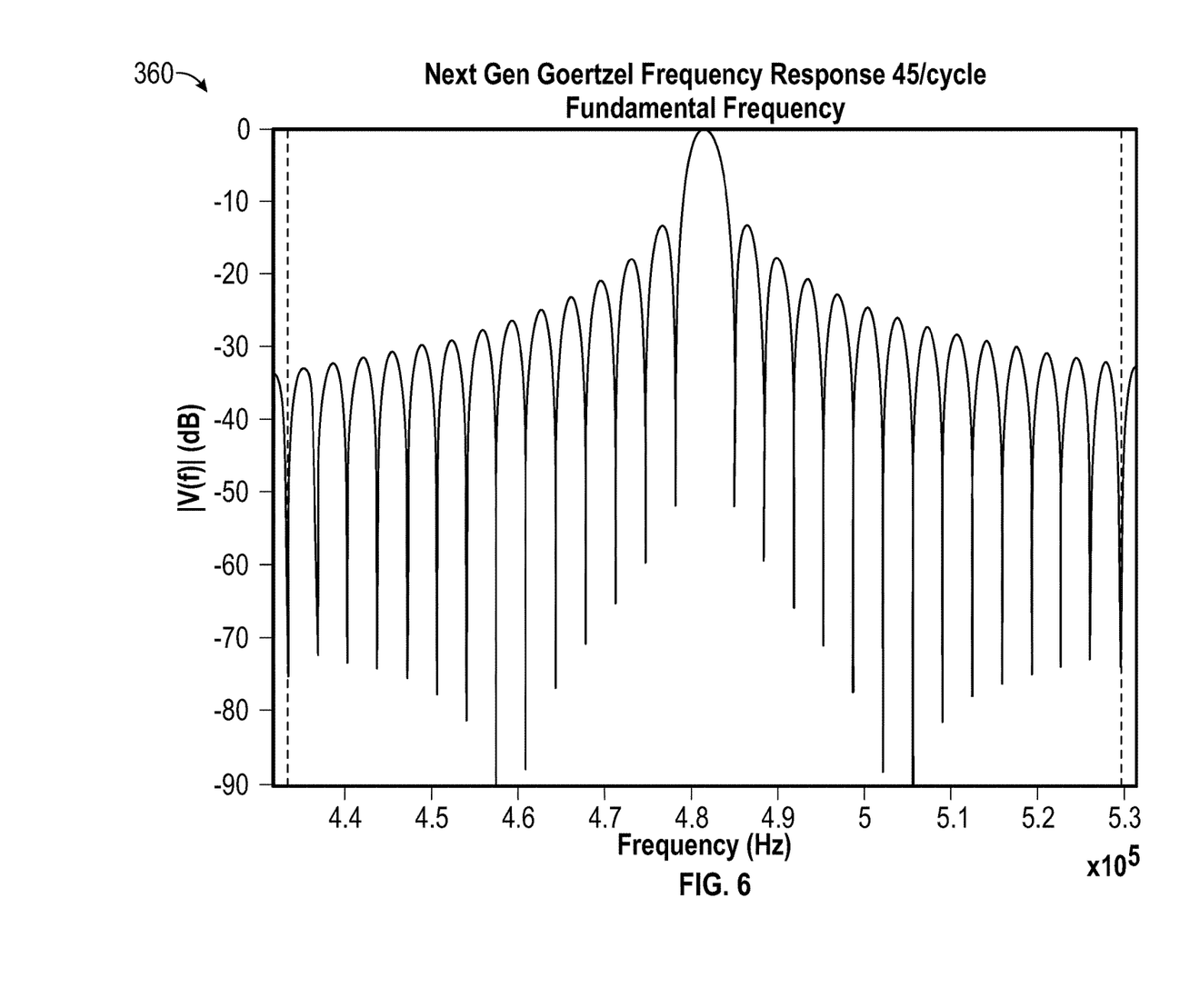
FIG. 6 is a frequency response plot of discontinuous RF waveforms generated by the electrosurgical generator of FIG. 1 according to the present disclosure.

With reference to FIG. 6, which shows a frequency response plot 360 for discontinuous waveforms, a separate Goertzel filter is pointed at the base repetition rate as well as even and odd harmonics of the RF waveform being analyzed. As the fundamental frequencies are not completely orthogonal, there is overlap of certain harmonics. The overlap of sets of harmonics produce a discontinuity in the Goertzel array plot. This is used to detect if significant cross-conductance from one RF source is occurring in the sensors 216 or 316 of another RF source. If it is desired to separate the sources which include combined information in only 1 of a plurality of harmonics, the unimpacted harmonics are used in combination with a percentage of the impacted harmonics. The separated cross-conductance information is used as a dosage monitor to detect excessive cross-conductance situations.

In embodiments, where both the first and second RF waveforms are discontinuous, the limited frequency space may be constraining. Discontinuous waveforms may have a repetition rate from about 20 KHz to about 490 KHz. The repetition rate does not allow for a completely orthogonal solution from a signal processing standpoint. The technique for determining the power value for each of the first RF source 202 and the second RF source 302 to be used for independent control is dependent on the level of cross-conductance. Cross-conductance results in real power deposited at the contact impedance. Thus, the power to control is based on the sum of cross-conductance power deposited at the contact impedance site and port source power deposited at the contact impedance. In embodiments, power deposited in the non-contact tissue impedance and the return electrode pad 26 may also be included in the overall calibration of a specific RF port. If frequency discrimination is used for power control, prior to use the generator 100, the instruments 20' and 20", and the return electrode pad 26 are used in a calibration procedure, which takes into account both cable compensation for supply lines 24' and 24" and the return line 28 as well as harmonic overlap and cross-conductance. Cross-conductance may also be monitored as a mitigation to potential dosage errors.

In embodiments, where one the first and second RF waveforms is continuous while the other is discontinuous, the continuous RF waveform may be at the higher Goertzel frequency of about 481 KHz and the discontinuous RF waveform may be at a lower frequency of about 433 KHz, such that there is very little interference that happens between the sources due to the frequency response of the Goertzel being divisible by 45 (see FIG. 6) as well as the concentration of discontinuous energy at or below its carrier frequency of 433 KHz.

In embodiments, where the first and second RF waveforms are continuous, since the continuous waveforms are generally not a perfect sine wave, the pre-selected unique carrier frequencies of 433 KHz and 481 KHz also comply with coherent sampling rules used to separate the continuous RF sources in combination with a Goertzel filter to provide attenuation of the interfering constructive or destructive signal from the other source. A band pass filter provides a signal pass-band region and lower/upper signal rejection regions. The level of rejection is variable and based on the type of band pass filter designed. Finite impulse response (FIR) filters provide a sinc function (sin x/x) type magnitude vs frequency response. The implementation of a computationally efficient Goertzel filter acts like a sampling function as shown in plots 350 and 360 of FIGS. 5 and 6.

Figure 7:
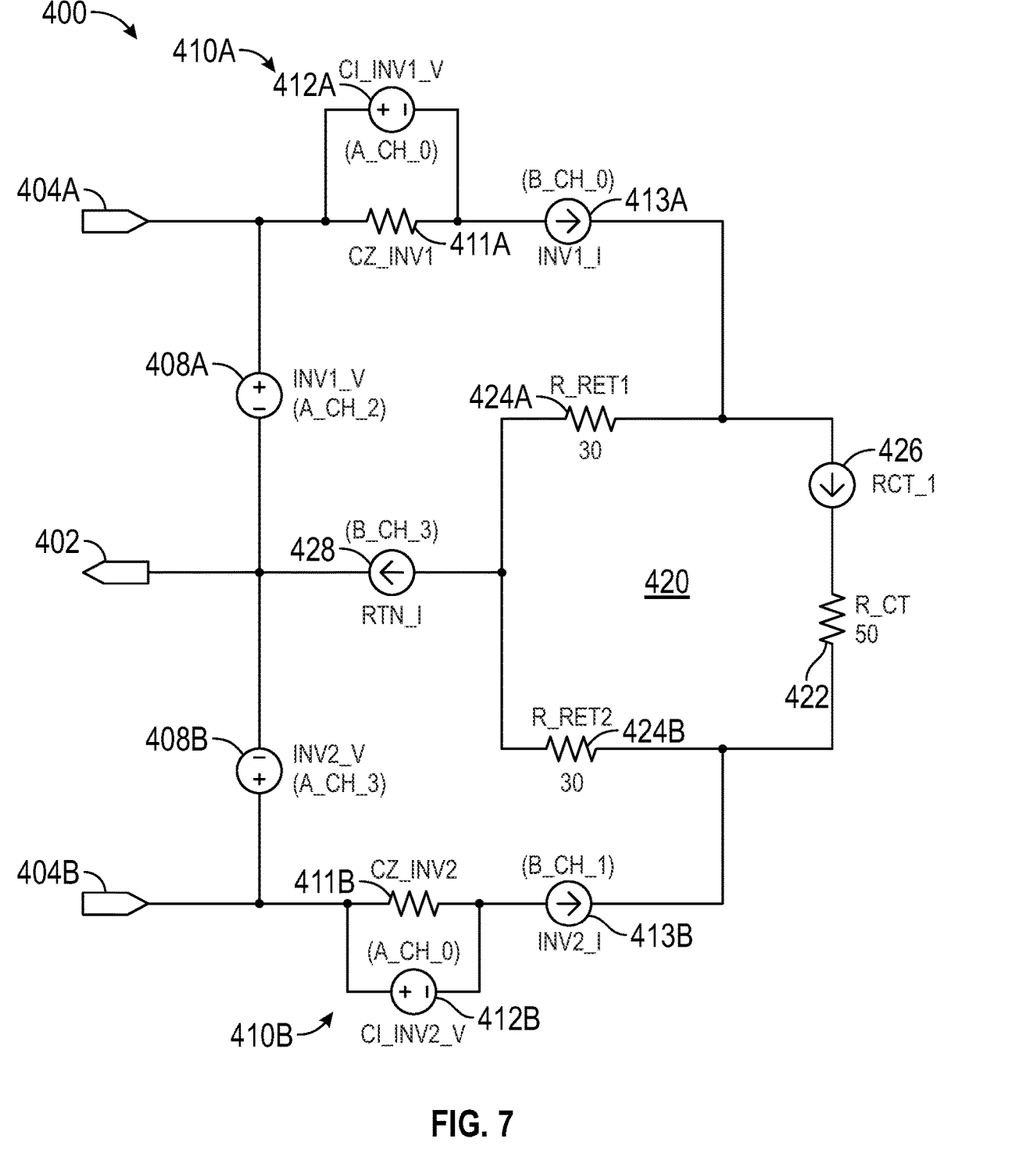
FIG. 7 is an electrical schematic of a calibration assembly for calibrating the electrosurgical generator of FIG. 1 according to the present disclosure.

With reference to FIG. 7, the generator 100 is calibrated using a calibration assembly 400, which includes a return connector 402 configured to couple to the port 118, which in turn, is coupled to the return terminal 312. The calibration assembly 400 also includes a first active connector 404a and a second active connector 404b, which are configured to couple to the ports 110 and 112 of the generator 100, which are in turn coupled to the active terminals 210 and 310 (FIG. 3).

The calibration assembly 400 includes a first voltage meter 408a and a second voltage meter 408b. The first voltage meter 408a is coupled in parallel with the return connector and the first active connector 404a and is configured to measure voltage therebetween. The second voltage meter 404b in parallel with the return connector and the second active connector 404b and is configured to measure voltage therebetween.

The calibration assembly 400 further includes a first contact impedance portion 410a and a second contact impedance portion 410b. The first and second contact impedance portions 410a and 410b simulate impedance where the active electrodes 23' and 23" of the monopolar electrosurgical instruments 20' and 20" contact tissue, namely, the point where tissue effect occurs during electrosurgery and where the power is applied by each of the RF sources 202 and 302. Each of the first and second contact impedance portions 410a and 410b includes a resistor 411a and 411b and a first contact voltage meter 412a and a second contact voltage meter 412b, respectively. The resistors 411a and 411b may have a resistance from about 10Ω and 50Ω to simulate tissue. The first and second contact voltage meters 412a and 412b are configured to measure voltage between input and output of the resistors 411a and 411b, respectively. Furthermore, each of the first and second contact impedance portions 410a and 410b is coupled to a first contact current meter 413a and a second contact current meter 413b, respectively, which are configured to measure current passing from the first and second contact impedance portions 410a and 410b.

The calibration assembly 400 also includes a return electrode impedance portion 420 having a resistor 422 configured to simulate tissue contacting the return electrode pad 26. The resistor 422 may have a resistance from about 10 Ohms (Ω) and 50Ω and represents the tissue electrical resistance between the contact impedances of each RF source 202 and 302. Furthermore, the return electrode impedance portion 420 also includes a pair of resistors 424a and 424b configured to simulate the foil electrodes 26a and 26b of the return electrode pad 26, respectively. The pair of resistors 424a and 424b may have a resistance of about 30Ω.

The resistors 424a and 424b represent the resistance of the contact between each of the foil electrodes 26a and 26b of the return electrode pad 26 and the tissue. Dual foil return electrodes are used to monitor contact quality and/or peel detection of the return electrode pad 26 as a safety mitigator against return electrode "pad" burns. Thus, the amount of dual activation cross conductance is related to the input impedance of each of the RF sources 202 and 302 as well as the amount of contact impedance present.

The return electrode impedance portion 420 also includes a tissue current meter 426 configured to measure current supplied to the resistor 422. The return electrode impedance portion 420 is also coupled to a return current meter 428, which measures current from the return electrode impedance portion 420 to the return connector 402. The resistance of each of the resistors 411a, 411b, 422, 424a, 424b may be fixed and may be from about 30 Ohms to about 50 Ohms based tissue being modeled. Fixed resistance allows for calibration to be done on either the contact impedance (resistance) or across the entire resistive load from the electrode contact point to REM return. The rationale for the fixed resistance values for 424a, 424b, and 422 is provided by a study of in-vivo tissue. The variability of resistor 422 provides little change to the calibration and current flowing to REM due to the parallel conductance paths present. That allows for keeping the resistor 422 fixed at about 50 Ohms. The measurements provided by the study of in-vivo tissue provide the validity of used fixed resistor values for 424A, 424B, and 422.

The resistance of each of the resistors 411a and 411b may be variable and may be adjustable by the calibration assembly 400 to allow for the calibration assembly 400 to simulate a variety of tissue impedances. Thus, poorly perfused adipose tissue may have a tissue electrical resistance somewhat higher than the resistance of 10Ω and 50Ω of the resistor 422, while highly perfused tissue such liver or bloody fields may have a lower tissue electrical resistance getting closer to 0Ω. Accordingly, the resistance of resistors 411a and 411b may be adjusted to achieve a desired impedance for calibration.

Figure 8:
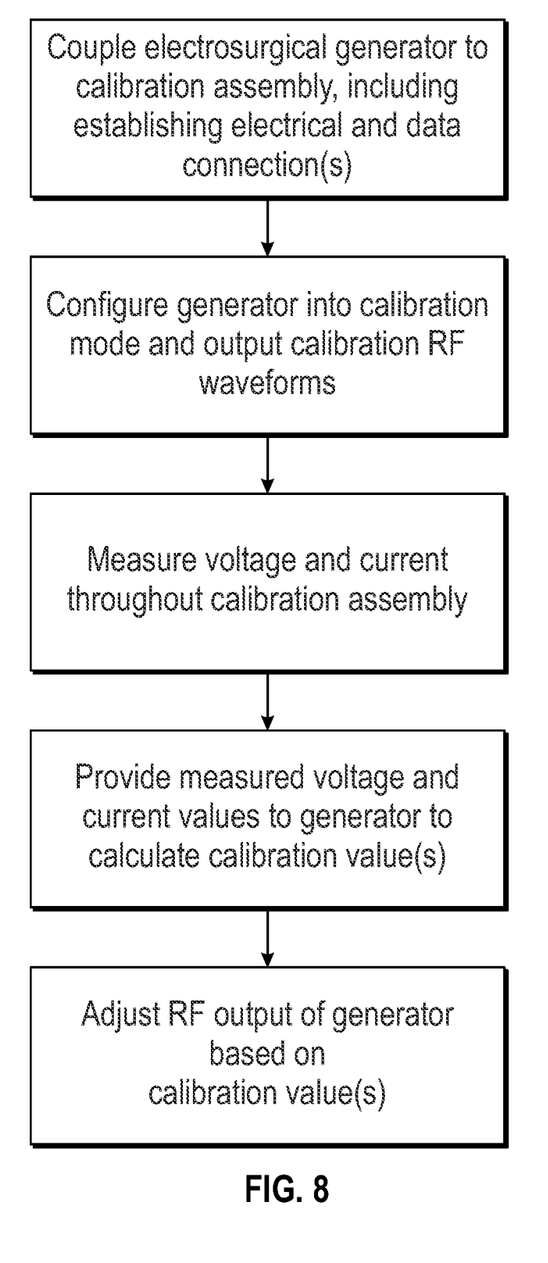
FIG. 8 is a flow chart of a method for calibrating the electrosurgical generator of FIG. 1 according to an embodiment of the present disclosure.

With reference to FIG. 8, which shows a method for calibrating the generator 100, prior to calibration, the electrosurgical generator 100 is coupled to the calibration assembly 400. In particular, the first and second active connectors 404a and 404b and the return connector 402 are coupled to the ports 110, 112, 118 of the generator 100. The coupling process may include providing a data interface either wired or wireless between the generator 100 and the calibration assembly 400, each of which may include any suitable communication circuitry for communicating with each other using any suitable communication protocol.

After coupling, the electrosurgical generator 100 is then entered into a calibration mode using the display 120. The calibration mode is configured to output a calibration RF waveform from each of first RF source 202 and the second RF source 302 of the generator 100 that is the same or similar to the RF waveforms output by the generator 100 during regular use. Once the calibration waveforms are supplied to the calibration assembly 400, the voltage meters 408a, 408b, 412a, 412b and the current meters 413a, 413b, 426, 426 output voltage and current values, respectively. The values are supplied to the generator 100, namely, the controllers 204 and 304, which then calculate and store calibration values in memory of the controllers 204 and 304. The calibration values may be specific to each of the first RF source 202 and the second RF source 302. The calibration values are used by the controllers 204 and 304 to adjust various parameters of the first and second RF waveforms to correct for any offsets between expected values and actual values as measured by the calibration assembly 400. Alternatively, or additionally, the calibration assembly 400 may also output the voltage and current values such that calibration values may be entered manually into the generator 100 through a user interface of the display 120.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope of the claims appended hereto.

What is claimed is:

1. An electrosurgical calibration system comprising:
   an electrosurgical generator including:
      a first radio frequency source having:
         a first power supply configured to output a first direct current waveform;
         a first radio frequency inverter coupled to the first power supply and configured to generate a first radio frequency waveform from the first direct current waveform;
         a first active terminal coupled to the first radio frequency inverter; and
         a first controller configured to control the first radio frequency inverter;
      a second radio frequency source including:
         a second power supply configured to output a second direct current waveform;
         a second radio frequency inverter coupled to the second power supply and configured to generate a second radio frequency waveform simultaneously as the first radio frequency waveform;
         a second active terminal coupled to the second radio frequency inverter; and
         a second controller configured to control the second radio frequency inverter; and
      a common return terminal coupled to the first radio frequency inverter and the second radio frequency inverter; and
   a calibration assembly including:
      a first active connector configured to couple to the first active terminal;
      a second active connector configured to couple to the second active terminal; and
      a return connector configured to couple to the common return terminal, wherein the calibration assembly is configured to measure at least one electrical property in response to the first and second radio frequency waveforms.

2. The electrosurgical calibration system according to claim 1, wherein the calibration assembly further includes:
   a first contact impedance portion configured to simulate impedance at a point of contact between tissue and a first electrosurgical instrument coupled to the first active terminal.

3. The electrosurgical calibration system according to claim 2, the first contact impedance portion includes a first resistor having a resistance from about 100 Ohms to about 2,000 Ohms.

4. The electrosurgical calibration system according to claim 1, wherein the calibration assembly further includes:
   a second contact impedance portion configured to simulate impedance at a point of contact between tissue and a second electrosurgical instrument coupled to the second active terminal.

5. The electrosurgical calibration system according to claim 4, the second contact impedance portion includes a second resistor having a resistance from about 100 Ohms to about 2,000 Ohms.

6. The electrosurgical calibration system according to claim 1, wherein the calibration assembly further includes return electrode impedance portion configured to simulate impedance at a point of contact between tissue and a return electrode pad coupled to the common return terminal.

7. The electrosurgical calibration system according to claim 6, wherein the return electrode impedance portion includes a pair of resistors configured to simulate a pair of foil electrodes of the return electrode pad.

8. The electrosurgical calibration system according to claim 1, wherein the calibration assembly includes a plurality of resistors configured to simulate impedance at points of contact between a return electrode pad to the common return terminal, a first electrosurgical instrument coupled to the first active terminal, and a second electrosurgical instrument coupled to the second active terminal.

9. The electrosurgical calibration system according to claim 8, wherein the plurality of resistors are variable resistors whose resistances are adjusted by the calibration assembly.

10. The electrosurgical calibration system according to claim 1, wherein the calibration assembly includes at least one sensor configured to measure an electrical property of the calibration assembly.

11. The electrosurgical calibration system according to claim 10, wherein each of the first controller and the second controller configured to calculate a calibration value based on the electrical property.

* * * * *